United States Patent [19]
Jones et al.

[11] Patent Number: 5,899,873
[45] Date of Patent: May 4, 1999

[54] BIOLOGICAL FLUID DELIVERY SYSTEM

[75] Inventors: Kenneth A. Jones, McKinney; Martyn Abbott; Andrew P. Mattson, both of Richardson, all of Tex.

[73] Assignee: Quest Medical, Inc., Allen, Tex.

[21] Appl. No.: 08/823,529

[22] Filed: Mar. 24, 1997

[51] Int. Cl.$^6$ ................................................. A61M 37/00
[52] U.S. Cl. ............................................. 604/4; 165/186
[58] Field of Search ........................... 604/4–6; 607/106; 165/67, 122, 186

[56] References Cited

U.S. PATENT DOCUMENTS

| | | | |
|---|---|---|---|
| 5,186,431 | 2/1993 | Tamari | 251/5 |
| 5,215,450 | 6/1993 | Tamari | 417/478 |
| 5,255,734 | 10/1993 | Leonard et al. | 165/96 |
| 5,388,634 | 2/1995 | Weinstein et al. | 165/78 |
| 5,403,281 | 4/1995 | O'Neill et al. | 604/113 |
| 5,429,483 | 7/1995 | Tamari | 417/307 |
| 5,514,095 | 5/1996 | Brightbill et al. | 604/113 |
| 5,585,007 | 12/1996 | Antanavich et al. | 210/782 |
| 5,674,190 | 10/1997 | Kelly | 604/4 |

*Primary Examiner*—John G. Weiss
*Assistant Examiner*—Ki Yong O
*Attorney, Agent, or Firm*—Sidley & Austin

[57] ABSTRACT

A cardioplegia system for delivering cardioplegic solution to the heart during open heart surgery in cooperation with an extracorporeal blood circuit employing a heart/lung machine, includes a conduit diverting a portion of the blood flow from the heart/lung machine to a cardioplegia delivery line. A heat exchanger assembly including a heat exchanger for controlling fluid temperature is provided in the cardioplegia delivery line. In addition to a heat exchanger, the heat exchanger assembly includes an integral bubble trap, filtration means and means to enable the measurement of certain physical characteristics of the circulating cardioplegia fluid and/or certain events occurring within the heat exchanger assembly.

39 Claims, 3 Drawing Sheets

BIOLOGICAL FLUID DELIVERY SYSTEM

BACKGROUND OF THE INVENTION

1. Field of the Invention

The invention relates to a fluid delivery system, and more particularly to a biological fluid delivery system having a sterile disposable assembly which interfaces with a plurality of sensors which are integrally apart of the fluid delivery system.

2. Background

In the performance of open heart surgery, the patient is supported by an extracorporeal blood circuit employing a heart/lung machine. The heart is isolated from the vascular system, and venous blood is diverted into the extracorporeal blood circuit where it is oxygenated, temperature-controlled, filtered and returned to the patient's arterial side. A separate circuit is established for supplying a cardioplegic solution to the heart as the surgery proceeds.

The cardioplegia circuit functions to still the heart, lower the metabolic requirements of the heart, protect the heart during periods of ischemia, and, finally, prepare the heart for reperfusion at the end of the procedure. Operation of the extracorporeal blood circuit as well as the cardioplegia delivery is performed by a trained perfusionist under the direction of the surgeon. The principal elements of cardioplegia solution are blood, representing a small fraction diverted from the output of the heart/lung machine, combined with a crystalloid solution. A minor but critical amount of potassium solution is added to the cardioplegic flow to still the heart. Still further, other fluid additives may be combined with the cardioplegia fluid as necessary to address particular patient conditions or procedure requirements.

Depending upon the requirements of the particular surgery, the cardioplegia solution may be cooled or warmed, and may be delivered in antegrade fashion to the aortic root, or in a retrograde mode to the coronary sinus. The requirements placed upon the cardioplegic solution vary as the surgery proceeds, and are subject to the clinical judgment of individual surgeons.

A typical cardioplegia delivery system employs two tubes routed through a single rotary peristaltic pump to forward both the separate blood and crystalloid solutions to a Y combining the two into a single flow. The ratio between the blood and crystalloid solution is determined simply by the relative diameters of the tubing carrying the two solutions, since each is mounted on the same rotary peristaltic mechanism and thus is forwarded by the same action. The tubing is usually provided in a 4:1 ratio of blood to crystalloid cross-sectional flow area, so that the rotary peristaltic pump is delivering blood and crystalloid to the delivery line in a ratio of approximately 4:1. Potassium is typically provided to the delivery line upstream of the pump from two alternate crystalloid solutions containing potassium, one having a relatively low concentration of potassium, the other a higher concentration. The perfusionist selects between the two sources to initiate or control an arrested state of a patient's heart. The higher potassium concentration is utilized to arrest the heart, while the lower is used to maintain the stilled condition. The clinical team must provide sufficient potassium in the cardioplegia solution to establish the stilled condition of the heart and maintain it during the procedure, while avoiding the risks associated with hyperkalemia which may result from excessive potassium.

Without regard to the specific protocol or technique employed, cardioplegia fluid delivery requires control of cardioplegia fluid temperature and pressure and the delivery of an air-free solution. Consequently, cardioplegia delivery systems employ pressure and temperature sensors; certain controls to adjust fluid temperature and pressure based on the data provided by said sensors (for example, heat exchangers); and other devices to filter the potentially dangerous air or gas bubbles from the cardioplegia fluid.

Current cardioplegia delivery systems do not provide integral pressure or temperature monitoring. With regard to pressure monitoring, the perfusionist is required to add a pressure sensor, or a pressure gauge, at a selected point within the fluid system, thus necessitating the assembly of additional sterile components which are costly and are subject to being assembled incorrectly. A fluid pressure isolator, a device which separates the sterile cardioplegia fluid from a nonsterile pressure sensor using a protective membrane, is commonly used in known cardioplegia systems. Fluid pressure isolators dampen the measured pressure due to air compliance within said devices. Temperature monitoring requires the addition of a temperature probe, in a conductive sheath, to be inserted into the system heat exchanger.

Cardioplegia delivery system heat exchangers typically use a temperature controlled water source across a thermally conductive medium to influence and adjust the temperature of the cardioplegia fluid. The temperature controlled water is pumped from warm or cold water reservoirs, the reservoirs being coupled to the heat exchanger, directly or indirectly through a holder. In addition to the physical configuration and its related impact on the efficiency of a heat exchanger, a number of system variables influence the device's effectiveness: the cardioplegia solution flow rate, the cardioplegia solution inlet temperature and the flow rate and temperature of the temperature controlled water. As current systems permit only the manual influence of the temperature of the water circulated through the heat exchanger, precise control of the delivery temperature of cardioplegia fluid is severely limited.

Various devices are utilized in an effort to remove potentially harmful gas bubbles from cardioplegia fluids (or other biological fluids) prior to delivery. One such device is a bubble trap. The bubble trap acts to separate, through fluid flow, any trapped gases within the fluid. As bubble traps are enclosed, the separated gas accumulates in the interior of the device. Current bubble trap devices have limited capacity and require manual venting. Consequently, the perfusionist must closely monitor and react when the bubble trap requires venting. An alternative design utilizes a microporous hydrophobic membrane to vent air from the system. Although initially effective, such membranes degrade when exposed to blood proteins vitiating the effectiveness of these devices.

A need is shown to provide an improved biological fluid delivery system which utilizes a sterile disposable component to combine the functions of temperature control, gas separation and/or filtration of a biological fluid. Moreover, the sterile disposable component must interface with a plurality of sensors, integral with the fluid delivery system, to allow the accurate, reliable measurement of certain fluid physical properties. The measurements made by said sensors will allow the fluid delivery system to modify the physical properties of the biological fluid or otherwise effect certain operations of the fluid delivery system.

SUMMARY OF THE INVENTION

The present invention is directed to a biological fluid delivery system. The system generally includes a biological fluid source and a patient delivery line, having a sterile disposable positioned therebetween. The sterile disposable has one or more stages capable of modifying the physical characteristics of the biological fluid, for example, temperature, gas content and particulate content. The sterile disposable further includes one or more sensor receiving receptacles. The sterile disposable is fixedly engaged by a mounting surface. The mounting surface incorporates one or more sensors which detect certain conditions or measure certain physical characteristics of the biological fluid which flows through the sterile disposable. When in an engaged position, the sensors of the mounting surface are fully received by and directly engaging the sensor receiving receptacles of the sterile disposable. The fluid delivery system further includes a microprocessor which is in communication with the sensors of the mounting surface as well as a number of control mechanisms. From information obtained from the one or more sensors, the microprocessor effects changes to the physical characteristics of the biological fluid and/or effect changes to the fluid delivery system for the safe, efficient and accurate delivery of the biological fluid to a patient.

An object of the present invention is to provide a sterile disposable which directly engages certain measurement devices and sensors of a fluid delivery system to allow for the direct, efficient and accurate measurement of fluid characteristics and/or detection of certain events or conditions.

Another object of the present invention is to provide a biological fluid delivery system having a process control loop by and between a central control microprocessor, a plurality of permanent sensors and a plurality of control mechanisms, where said sensors detect certain system conditions and measure certain fluid properties via a sterile disposable.

Another object of the present invention is to provide a sterile disposable featuring one or more stages, such stages permitting accurate, efficient temperature control of the biological fluid passing therethrough, separation of gas from the biological fluid and/or fluid filtration to remove hazardous emboli.

Another object of the present invention is to provide a fluid delivery system having a sterile disposable, wherein the fluid delivery system can detect an unsafe level of gas accumulation in the sterile disposable and automatically vents such gas.

Other objects and advantages of the present invention will be apparent to those of ordinary skill in the art having reference to the following specification together with the drawings.

BRIEF DESCRIPTION OF THE DRAWINGS

For a more complete understanding of the present invention and for further advantages thereof, reference is now made to the following Description of the Preferred Embodiments taken in conjunction with the accompanying drawings in which.

DESCRIPTION OF THE PREFERRED EMBODIMENTS

Figure 1:
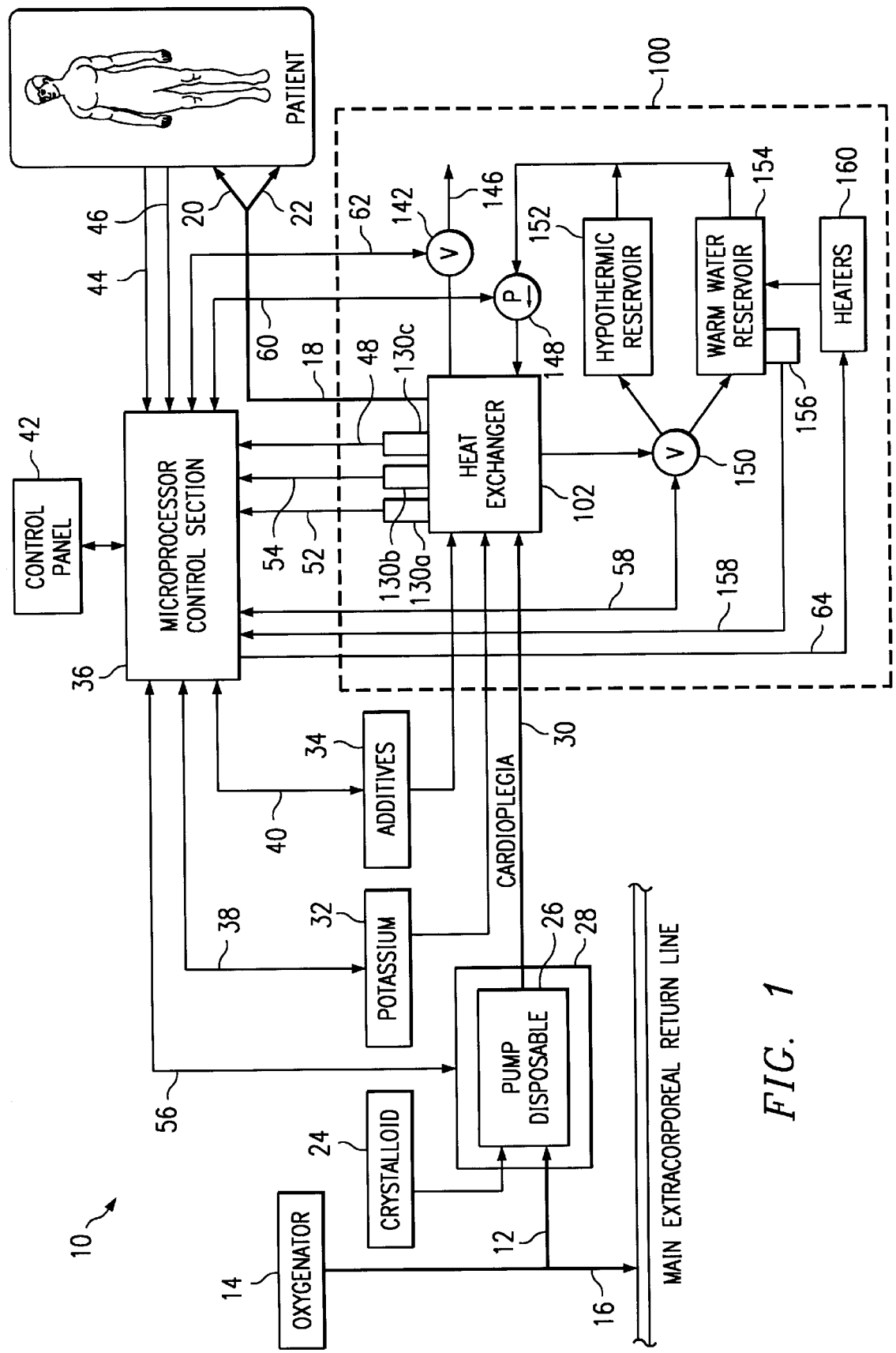
FIG. 1 is a schematic diagram of a cardioplegia delivery system embodying the invention.

As depicted in FIG. 1, a cardioplegia delivery system 10 is established to provide solution to the heart of a patient during open heart surgery. The principal component of the cardioplegic solution is blood delivered to the system through conduit 12 which is connected to the output of an oxygenator 14 of a heart/lung machine sustaining the patient's vascular system while the heart is isolated during surgery. Oxygenator 14 provides arterial blood to the main extracorporeal circuit through a return line 16 to the patient's aorta. A fraction, usually about 10%, of the heart/lung machine output is diverted into conduit 12 for processing by the cardioplegic circuit and, ultimately, forwarding to the patient's heart through cardioplegia delivery line 18. The cardioplegic solution flowing through line 18 may be delivered through antegrade line 20 to a heart's aortic root, or through retrograde line 22 to a heart's coronary sinus.

A crystalloid solution is stored in container 24 for possible combination with blood flowing in line 12. Combination of these fluids occurs in a disposable pumping cassette 26. In the preferred embodiment, pumping cassette 26 shall be of configuration generally consistent with that disclosed in U.S. Pat. No. 5,588,816, such disclosure being incorporated by reference here. Pump cassette 26 is mounted in and subject to the operations of an electromechanical pump mechanism 28. In the preferred embodiment, pump mechanism 28 shall be of a configuration generally consistent with that disclosed in U.S. patent application Ser. No. 08/563,202, filed Nov. 27, 1995, such disclosure being incorporated by reference here.

The output of cassette 26 is supplied through line 30 to a heat exchanger assembly 102. In the preferred embodiment, a second pump 32, delivering a potassium solution, and/or a third pump 34, delivering other fluid additives, may also be supplied to heat exchanger assembly 102. Heat exchanger assembly 102, described in detail below, serves among other functions to combine those fluids supplied thereto.

Preferably, pumps 32, 34 are single chamber, positive displacement pumps of a configuration similar in structure and operation to that of pump mechanism 28. Pumps 32, 34 are independently controlled by microprocessor control section 36 via signal paths 38, 40, respectively. As the solutions delivered by pumps 32, 34 can be of a critical nature, the preferred pumps 32, 34 allow for the accurate control and combination of potassium and/or other fluid additives with the cardioplegia fluid. Pumps 32, 34 dispense their respect fluids at flow rates less than about 10%, and preferably less than about 5%, of the total flow rate issuing from pump cassette 26. Although the preferred embodiment utilizes heat exchanger assembly 102 to combine the cardioplegia fluid from pump cassette 26 and the fluids of pumps 32, 34, one ordinarily skilled in the arts shall understand that the fluids from pumps 32, 34 may be introduced at any point along the fluid path continuum from source to delivery site.

Data input to microprocessor 36 through control panel 42 may include an advantageous combination of the following parameters:

1. desired overall volumetric flow rate through disposable pump cassette 26;
2. desired blood/crystalloid ratio to be forwarded by disposable pump cassette 26;
3. desired potassium concentration to be established by pump 32;
4. desired additive concentration to be established by pump 34;

5. desired temperature of solution in cardioplegia delivery line 18; and
6. safety parameters such as the pressure of the cardioplegia solution in the system or in the patient.

The system includes patient monitoring of myocardial temperature along the signal path 44 and heart pressure along signal path 46 communicating to microprocessor control section 36. In addition, the pressure and temperature of the cardioplegic solution in delivery line 18 is sensed (via pressure sensor 130*a* and temperature sensor 130*b*) and the corresponding data forwarded along respective signal paths 52 and 54 to control section 36.

In response to the data input through control panel 42 and the monitored conditions along signal paths 44, 46, 52 and 54, control section 36 effects the control of the operation of (i) pump mechanism 28 via signal path 56, (ii) potassium pump 32 by signal along path 38; and (iii) additives pump 34 by signal along path 40. In addition, microprocessor control section 36 controls the heat exchanger circuit 100 along signal paths 58, 60, 62, 64, which will be discussed in greater detail below, for obtaining a desired cardioplegia delivery temperature. Further, control panel 42 allows parameters such as pressure limits for a particular procedure or a particular patient to be controlled based upon input settings or based upon preset standards (for example, one range of acceptable pressure limits for antegrade and another range for retrograde cardioplegia).

In accordance with the invention, the microprocessor controller section 36 controls pump mechanism 28 to combine crystalloid from container 24 and blood from line 12 in any selected ratio over a broad range of blood/crystalloid ratios. A preferred range for the blood/crystalloid ratio adjustment capability is from 0 to 20:1. Notwithstanding, an operator can direct system 10 to deliver blood with no crystalloid and, conversely, crystalloid with no blood.

The rate of fluid flow from pump mechanism 28 is preferably variable from 0 to 500 milliliters per minute. Pump mechanism 28 may be operated by microprocessor 36 in either a continuous or intermittent mode by instruction through control panel 42. If selected for delivery of fluid, pumps 32, 34 are automatically controlled to deliver at a rate such that the introduction of potassium solution (or other fluid additive, if any) to the cardioplegia fluid is automatically maintained at the selected concentration vis-à-vis the flow from disposable cassette 26 without regard to changes made to the flow rate from pump cassette 26 or changes in the blood/crystalloid ratio.

Referring to heat exchanger circuit 100, circuit 100 includes heat exchanger assembly 102 and a circulation system to enable the responsive heating and cooling of the cardioplegia fluid.

Figure 2:
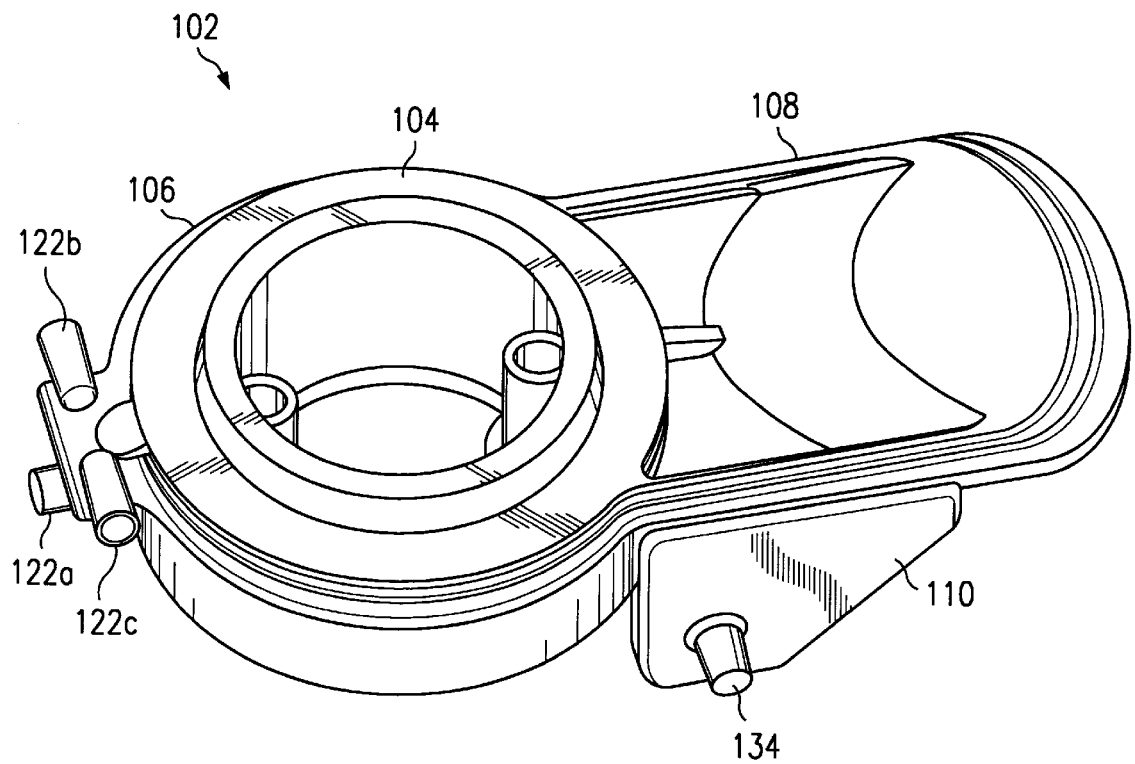
FIG. 2 is a perspective view of a heat exchanger in the system of FIG. 1.
Figure 3:
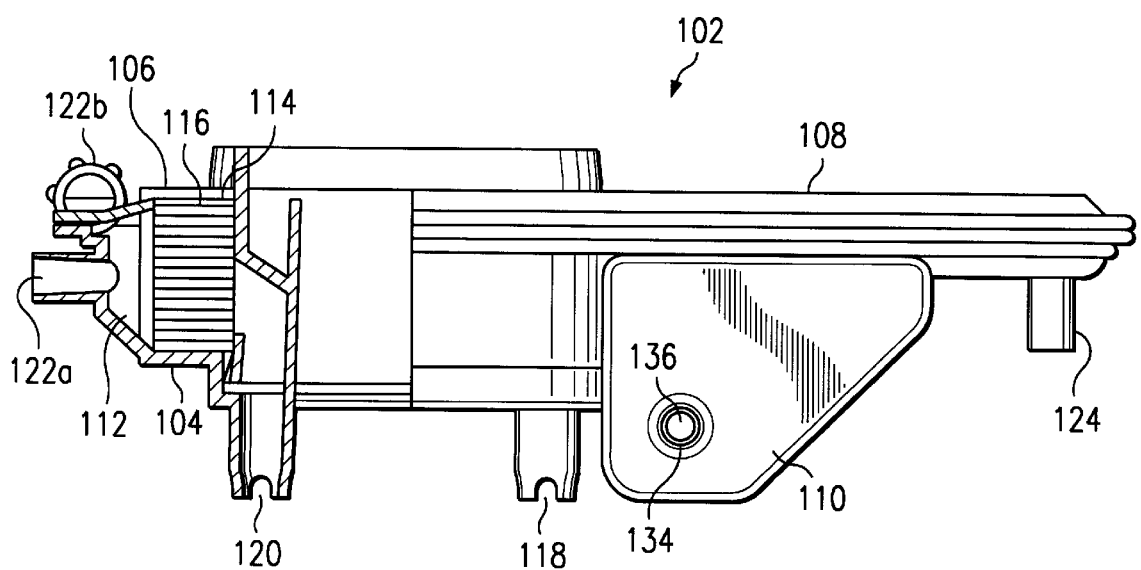
FIG. 3 is a partial sectional view of the right side of the heat exchanger of FIG. 2.
Figure 4:
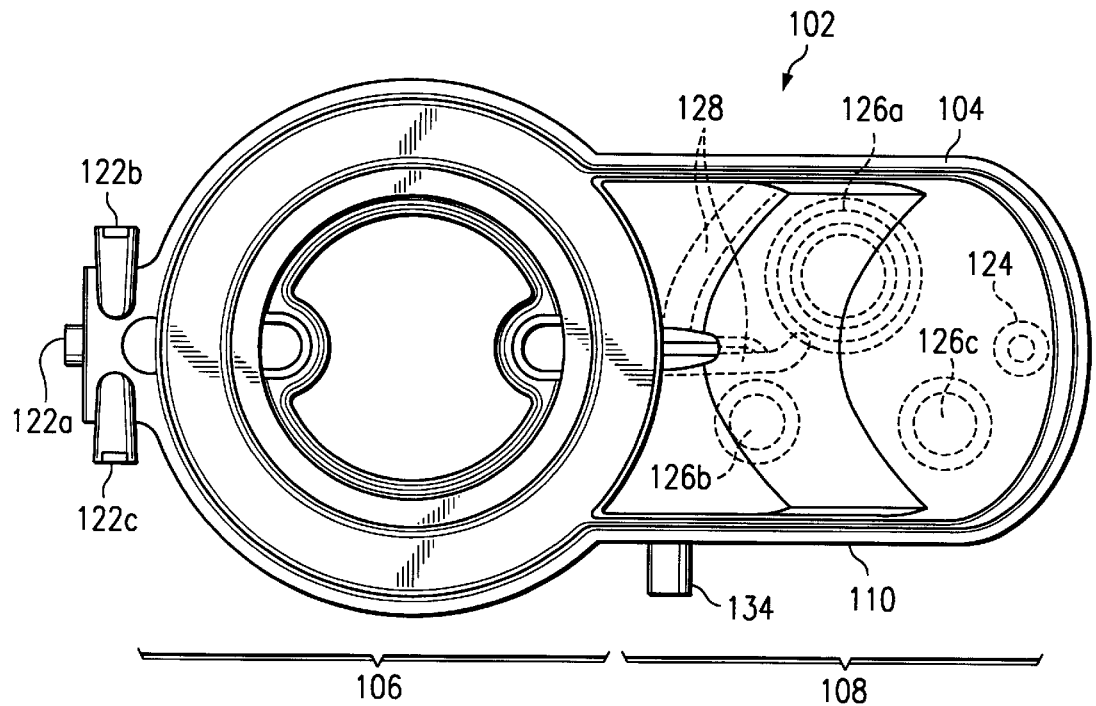
FIG. 4 is a plan view of the heat exchanger of FIG. 2.

FIGS. 2, 3 and 4 illustrate the preferred embodiment of heat exchanger assembly 102. In addition to serving as a means for controlling the temperature of the fluid that passes therethrough, heat exchanger assembly 102 functions as a filtration means, gas separator and a vehicle to allow the measurement of various cardioplegia fluid properties.

Heat exchanger assembly 102 includes a rigid exterior 104 defining the various regions of said assembly. Specifically, heat exchanger assembly 102 comprises three integrated regions: heat exchanger region 106; bubble trap 108 and exit region 110.

Heat exchanger region 106 comprises cardioplegia fluid circulation chamber 112 and temperature controlled fluid circulation chamber 114. Cardioplegia fluid circulation chambers 112 is hermetically separate and distinct from temperature controlled fluid circulation chamber 114. Bellows 116 separates the two circulation chambers. Bellows 116 is constructed of a material conducive to the transfer of heat energy and resistant to biological fluid attack (for example, stainless steel). Temperature controlled fluid circulation chamber 114 includes inlet 118 and outlet 120. Cardioplegia fluid circulation chamber 112 includes multiple inlets 122*a*, 122*b*, 122*c* respectively coupled to the output from pumps 28, 32, 34. Chamber 112 opens into bubble trap 108.

Bubble trap 108 is an enclosed region which permits the accumulation of air, or other gases, during the circulation of fluid through heat exchanger assembly 102. Bubble trap 108 includes a vent outlet 124 to allow the expulsion of said accumulated gases. Bubble trap 108 also includes a plurality of sensor receptacles 126*a*, 126*b*, 126*c* formed into the lower surface of assembly 102. The interior configuration of bubble trap 108, which includes the specific placement of sensor receptacles 126*a*, 126*b*, 126*c* and/or flow guides 128, serve to minimize fluid flow effects across sensor receptacles 126*a*, 126*b*, 126*c* to avoid inaccuracies and incorrect measurements of fluid properties (see FIG. 4).

In the preferred embodiment, receptacles 126*b*, 126*c* are formed into the lower surface of assembly 102 and designed to complement the exterior of sensors 130*b*, 130*c* to insure accurate sensor operation. Receptacle 126*a*, which receives pressure sensor 130*a* in an operational position, comprises a flexible membrane (not shown) to allow accurate pressure communication directly with sensor 130*a*. The flexible membrane, formed from PVC film or the like, is attached to assembly 102 by adhesive joint or other process well known to those having ordinary skill in the art. Bubble trap 108 directs fluid flow into exit region 110.

Exit region 110 includes outlet port 134. Exit region 110 may also incorporate an emboli filtration means 136. In the preferred embodiment, exit region 110 includes a 160 micron filtration screen for removing any emboli greater than 160 microns.

Figure 5:
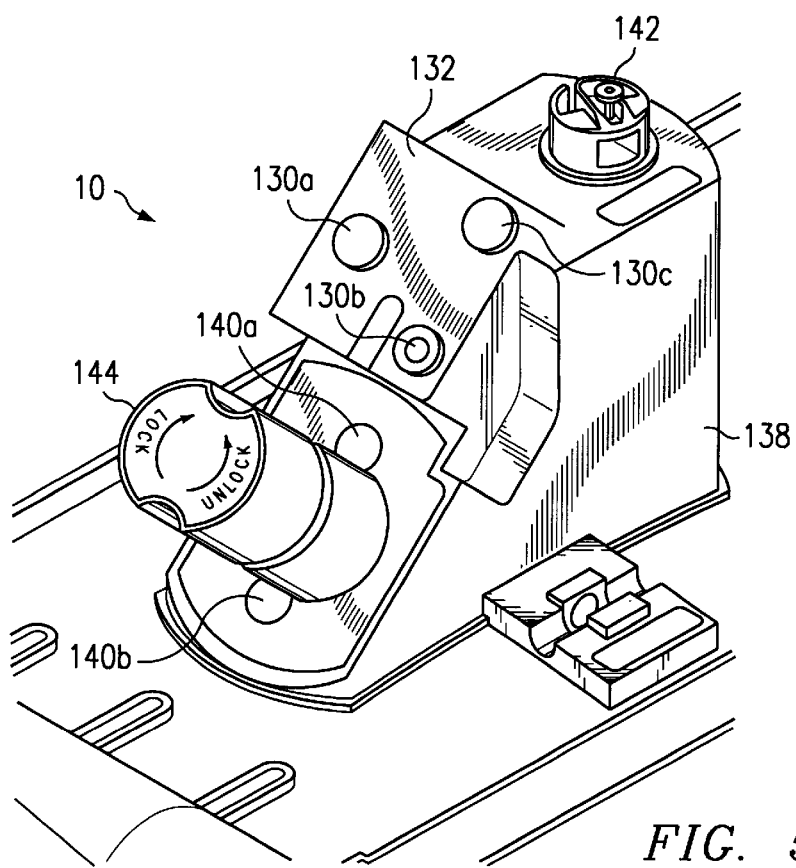
FIG. 5 is partial perspective view of one embodiment of the cardioplegia delivery system of FIG. 1.

Referring to FIG. 5, cardioplegia delivery system 10 includes heat exchanger mounting block 138. Heat exchanger mounting block incorporates sensor plate 132; temperature controlled fluid circulation ports 140*a*, 140*b*; vent valve means 142 and locking means 144. Sensor plate 132 maintains pressure sensor 130*a*, infrared temperature sensor 130*b* and ultrasonic level sensor 130*c*. The specific sensors identified herein are merely an example of the preferred embodiment, one ordinarily skilled in the art shall appreciate that other types of sensors or the like may be used to effect the intended purpose of the present invention.

Heat exchanger assembly 102 is positioned on mounting block 138 and locked into place with locking means 144. As discussed above, sensor receptacles 126*a*, 126*b*, 126*c* receive sensors 130*a*, 130*b*, 130*c*, respectively, when assembly 102 is locked into position. Likewise, inlet 118 and outlet 120 engage circulation ports 140*a*, 140*b*, respectively. Inlet 122*a* of heat exchanger assembly 102 is coupled to line 30, inlet 122*b* is coupled to the outlet of second pump 34, and inlet 122*c* is coupled to the outlet of third pump 32. Vent line 146 is coupled to vent outlet 124 and passes through vent valve means 142. Line 18 is coupled to outlet port 134.

Operationally, cardioplegia fluid is circulated across the exterior surface of bellows 116 while a temperature controlled fluid is circulated across the interior surface of bellows 116 to effect temperature control of the cardioplegia fluid. Pump 148 circulates temperature controlled fluid through heat exchanger assembly 102 either by push or pull. FIG. 2 depicts a "push through" coolant system in which pump 148 circulates the temperature controlled fluid through heat exchanger assembly 102 and then to two-way valve 150. Valve 150 directs, subject to the direction of microprocessor 36, the circulating fluid either to hypothermic reservoir 152 or warm water reservoir 15. Hypothermic reservoir 152 may consist of a reservoir containing a water-ice solution. Warm water reservoir 154 may consist of an internal reservoir having one or more sensors 156 and one or more heaters 160. Microprocessor 36 controls heaters 160 in accordance with that specified by control panel 42 and the measured data received from sensors 156.

As described above, sensors 130a, 130b, 130c provide information to the central microprocessor control section 36. Control section 36 utilizes said information for making adjustments, for example, adjusting the delivery flow rate to attain a particular pressure, adjusting valve 150 to select between heating and cooling the cardioplegia fluid, or, as immediately described above, the process for maintaining the temperature of the warm water reservoir 154. Likewise, control section 36 uses that information provided by sensor 130c, via signal path 48, to automatically open and close vent valve means 142 to expel any accumulated gases.

For some applications, where the fluid delivery system disclosed here does not require a heat exchanger stage, heat exchanger assembly 102 may comprise merely the bubble trap stage 108. An example of such application is the fluid delivery system 10 serving as a cardiopulmonary bypass machine.

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

We claim:

1. A biological fluid delivery system, having a microprocessor, to modify a physical characteristic of a biological fluid, the physical characteristic including at least one of a fluid temperature, a fluid gas content, and fluid emboli content, the system comprising:
   a biological fluid source;
   a patient delivery line;
   a disposable cassette, coupled between the fluid source and the patient delivery line so as to define a continuous flow path for a biological fluid, having a first stage capable of modifying the physical characteristic of the biological fluid and at least one sensor interface; and
   a fixed mount, having at least one sensor electrically coupled to the microprocessor, to engage and retain the disposable cassette when the system is in an operational state, wherein, in such state, the at least one sensor is received by a sensor interface of the disposable cassette.

2. The fluid delivery system of claim 1, wherein the fluid delivery system is a cardiopulmonary bypass machine, and the first stage of the disposable cassette is a gas removal stage.

3. The fluid delivery system of claim 1, wherein the fluid delivery system is a cardioplegia delivery system, and the biological fluid is cardioplegia.

4. The fluid delivery system of claim 3, wherein the first stage of the disposable cassette is a gas separation stage, and the disposable cassette further comprises a gas outlet.

5. The fluid delivery system of claim 3, wherein the disposable cassette further comprises a second stage, integrally formed with and extending from the first stage.

6. The fluid delivery system of claim 5, wherein the first stage is a heat exchanger stage and the second stage is a gas separation stage, and the disposable cassette further comprises a gas outlet.

7. The fluid delivery system of claim 5, wherein the disposable cassette further comprises a third stage, integrally formed with and extending from the second stage.

8. The fluid delivery system of claim 7, wherein the third stage is a filtration stage.

9. The fluid delivery system of claim 1, wherein at least one sensor senses and measures a fluid temperature of the biological fluid within the disposable cassette.

10. The fluid delivery system of claim 1, wherein at least one sensor senses and measures a fluid pressure of the biological fluid within the disposable cassette.

11. The fluid delivery system of claim 1, wherein at least one sensor senses an accumulation of gas within the disposable cassette.

12. The fluid delivery system of claim 1, further comprising a fluid circulation circuit having an inlet and an outlet integrated into said fixed mount.

13. The fluid delivery system of claim 12, wherein the disposable cassette releasably engages the inlet and the outlet of the fluid circulation circuit when in the operational state.

14. A biological fluid delivery system having a microprocessor and a plurality of sensors, said sensors being in direct communication with the microprocessor, for detecting certain conditions, measuring certain physical characteristics, or modifying certain physical characteristics of a biological fluid, the characteristics including at least one of a fluid temperature, a fluid gas content, and fluid emboli content, the system comprising:
   a biological fluid source;
   a patient delivery line;
   a disposable cassette, coupled between the fluid source and the patient delivery line and defining a continuous flow path for the biological fluid, having a first stage capable of modifying the physical characteristics of the biological fluid and at least one sensor receptacle;
   a fixed mounting surface, to engage and retain the disposable cassette when the system is in an operational state and carry the plurality of sensors, wherein, in such state, at least one of the plurality of sensors is fully received by a sensor receptacle of the disposable cassette; and
   a plurality of control mechanisms coupled and responsive to the microprocessor.

15. The fluid delivery system of claim 14, wherein the first stage of the disposable cassette is a gas separation stage, and the disposable cassette further comprises a gas outlet.

16. The fluid delivery system of claim 14, wherein the disposable cassette further comprises a second stage, integrally formed with and extending from the first stage.

17. The fluid delivery system of claim 16, wherein the first stage is a heat exchanger stage and the second stage is a gas separation stage, and the disposable cassette further comprises a gas outlet.

18. The fluid delivery system of claim 16, wherein the disposable cassette further comprises a third stage, integrally formed with and extending from the second stage.

19. The fluid delivery system of claim 18, wherein the third stage is a filtration stage.

20. The fluid delivery system of claim 15, wherein at least one of the plurality of control mechanisms effects a modification of the physical characteristics of the biological fluid responsive to a directive from the microprocessor, such directive being dependent upon sensor input to the microprocessor in a process control loop.

21. The fluid delivery system of claim 20, wherein at least one sensor detects and measures a fluid temperature of the biological fluid within the disposable cassette.

22. The fluid delivery system of claim 20, wherein at least one sensor detects and measures a fluid pressure of the biological fluid within the disposable cassette.

23. The fluid delivery system of claim 20, wherein at least one sensor detects an accumulation of gas within the disposable cassette.

24. The fluid delivery system of claim 20, further comprising a vent adapted to control the gas outlet of the disposable cassette.

25. The fluid delivery system of claim 24, wherein at least one of the plurality of control mechanisms controls the vent responsive to a directive from the microprocessor.

26. The fluid delivery system of claim 14, further comprising a temperature-controlled fluid circulation circuit having an inlet and an outlet integrated into said fixed mounting surface.

27. The fluid delivery system of claim 26, wherein the disposable engages the inlet and outlet of the temperature-controlled fluid circulation circuit when in the operational state.

28. A cardioplegia fluid delivery system having a microprocessor and a plurality of integrated sensors, said sensors being coupled to and in communication with microprocessor, for detecting certain conditions or measuring certain physical characteristics of a cardioplegia fluid, the physical characteristics including at least one of a fluid temperature, a fluid gas content, and fluid emboli content, the system comprising:

a cardioplegia fluid source;

a patient delivery line;

a controlled temperature fluid circulation circuit;

a sterile disposable cassette, coupled between the cardioplegia fluid source and the patient delivery line, having a first stage capable of modifying the physical characteristics of the cardioplegia fluid, a gas outlet and at least one sensor receiving receptacle;

a fixed mount supporting at least one of the plurality of sensors and releasably securing the disposable cassette in an operational position, such operational position coupling the disposable cassette to the controlled temperature fluid circulation circuit and positively engaging the sensor receptacles with the at least one of the plurality of sensors; and a plurality of control mechanisms coupled to and in communication with the microprocessor, the control mechanisms, microprocessor, and sensors forming a process control loop.

29. The fluid delivery system of claim 28, wherein the first stage of the disposable cassette is a gas separation stage.

30. The fluid delivery system of claim 29, wherein the disposable cassette further comprises a second stage, integrally formed with and extending from the first stage.

31. The fluid delivery system of claim 30, wherein the first stage is a heat exchanger stage and the second stage is a gas separation stage, and the disposable cassette further comprises a gas outlet.

32. The fluid delivery system of claim 28, wherein at least one of the plurality of control mechanisms effects a modification of the physical characteristics of the cardioplegia fluid responsive to a directive from the microprocessor.

33. The fluid delivery system of claim 32, wherein at least one sensor detects and measures a fluid temperature of the cardioplegia fluid within the disposable cassette.

34. The fluid delivery system of claim 32, wherein at least one sensor detects and directly measures a fluid pressure of the cardioplegia fluid within the disposable cassette.

35. The fluid delivery system of claim 33, wherein at least one sensor detects an accumulation of gas within the disposable cassette.

36. The fluid delivery system of claim 35, wherein the disposable cassette further includes a gas outlet, and at least one control mechanism is a vent controller coupled to and automatically controlling the gas outlet of the disposable cassette responsive to a signal from the microprocessor.

37. The fluid delivery system of claim 28, wherein the cardioplegia fluid comprises blood.

38. The fluid delivery system of claim 28, wherein the disposable cassette further comprises a filtration means.

39. A biological fluid delivery system for delivering a biological fluid having a microprocessor, the system comprising:

a biological fluid source;

a patient delivery line;

a controlled temperature fluid circulation circuit;

a disposable cassette, coupled between the biological fluid source and the patient delivery line, having a first stage and a second stage capable of modifying physical characteristics of the biological fluid and at least one sensor receiving receptacle, wherein the physical characteristics include at least one of a fluid temperature, a fluid gas content, and fluid emboli content;

a mount to receive and fixedly secure the disposable cassette in an operational position, having a plurality of integrated sensors, said sensors being coupled to and in communication with the microprocessor, for detecting certain conditions or measuring certain physical characteristics of the biological fluid, where in the operational position the disposable cassette is coupled to the controlled temperature fluid circulation circuit and effects engagement of the sensor receiving receptacles with the plurality of sensors; and a plurality of control mechanisms coupled to and in communication with the microprocessor, the control mechanisms, microprocessor and sensors forming a process control loop.

* * * * *